US 6,727,196 B2

United States Patent
Yahiaoui et al.

(10) Patent No.: US 6,727,196 B2
(45) Date of Patent: Apr. 27, 2004

(54) SURFACTANT SYSTEMS FOR PERSONAL CARE PRODUCTS

(75) Inventors: Ali Yahiaoui, Roswell, GA (US); Bernard Cohen, Berkeley Lake, GA (US); Joel Brostin, Alpharetta, GA (US); Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 97 days.

(21) Appl. No.: 09/944,774

(22) Filed: Aug. 31, 2001

(65) Prior Publication Data

US 2002/0069988 A1 Jun. 13, 2002

Related U.S. Application Data

(60) Provisional application No. 60/254,213, filed on Dec. 8, 2000.

(51) Int. Cl.$^7$ .............................. B32B 5/02; B32B 9/04; B32B 27/02; A61F 13/15; A61F 13/20
(52) U.S. Cl. ................. 442/118; 442/152; 442/153; 442/164; 442/165; 442/170; 442/171; 442/172; 604/359; 604/360; 604/364; 604/367; 604/370
(58) Field of Search ............................... 442/118, 152, 442/153, 164, 165, 170–172; 604/359, 360, 364, 367, 370

(56) References Cited

U.S. PATENT DOCUMENTS 5,728,081 A 3/1998 Baer et al.

FOREIGN PATENT DOCUMENTS

| WO | 99/63046 | 12/1999 |
| WO | 00/00231 | 1/2000 |
| WO | 00/50098 | 8/2000 |
| WO | 00/50099 | 8/2000 |

OTHER PUBLICATIONS

International Search Report dated Aug. 26, 2002, for International Application No. PCT/US01/45207.

Primary Examiner—Cheryl A. Juska
Assistant Examiner—Lynda Salvatore
(74) Attorney, Agent, or Firm—William W. Letson; Christos S. Kyriakou (57) ABSTRACT

The present invention relates to a composite material including a substrate with a first and a second layer, and a surfactant. The surfactant is applied to the first layer of the substrate. The surfactant acts to lower the surface tension of a fluid which contacts the first layer of the substrate such that the fluid is allowed or more readily enabled to pass through the first layer of the substrate, but such that the surfactant does not substantially adversely effect the absorption capacity or wicking height of the second layer of the substrate, as the second layer of the substrate substantially inactivates the surfactant upon contact or interaction therewith.

49 Claims, 1 Drawing Sheet

SURFACTANT SYSTEMS FOR PERSONAL CARE PRODUCTS

This application claims priority from U.S. Provisional Application No. 60/254,213 filed Dec. 8, 2000.

FIELD OF THE INVENTION

This invention relates to the use of surfactents which may be inactivated or degraded upon contact with one or more materials possibly in one or more layers of a substrate. The composite material includes a surfactant that can be applied to a substrate such as a nonwoven web such that the surfactant reduces the surface tension of a fluid so that the fluid intake into the substrate is enhanced and such that the surfactant is inactivated upon contacting or passing into another portion of the substrate.

BACKGROUND OF THE INVENTION

Surfactants are well-known compounds that are used in many fields to provide low surface tension to water or other fluids resulting in increased wettability, spreadability, emulsification, dispersion, penetration, and/or improved adhesion. Some surfactants also are known to impart softness characteristics to certain products, such as tissue.

While surfactants may produce a number of desired properties and benefits, prior usage of articles containing surfactants or having surfactants on the surface of the substrate reveals that surfactants frequently have adverse effects on the properties of the materials and/or surroundings to which the surfactants pass. For example, a surfactant is most commonly applied to a surface of a substrate in anticipation of fluid contact; however, after the surfactant is contacted by a fluid, some or all of the surfactant typically dissolves in the fluid and flows into the substrate with the fluid. The presence of the surfactant in the fluid in the substrate may result in reduced fluid flow (wicking) through the substrate due to reduced fluid surface tension which reduces capillary pressure. That is, if the substrate contains a surfactant the surfactant will enhance the passage of a contacting fluid into the substrate. However, the presence of the surfactant in the fluid reduces the wicking force (speed) end thus the substrate directly under the liquid penetration point can become saturated. This saturation will restrict the passage of more fluid into the substrate which may result in leakage and, an undesirable appearance of the product or even adverse contact with the skin of the wearer. The presence of a superabsorbent in the substrate magnifies the problem. As the surfactant containing fluid is being wicked at a slower rate, the fluid has a longer residency time near the superabsorbent near the fluid entry location into the substrate. These superabsorbent particles continue to swell and absorb fluid which eventually will lead to "gel blocking". More specifically, the phenomenon of gel blocking describes the tendency of hydrogel materials or so-called "superabsorbent materials" to swell in place once wetted and produce gelatinous material which blocks further transmission of the fluid being absorbed. The gelatinous material not only effects the fluid intake or absorption properties or the superabsorbent material, but also inhibits the wicking and dispersion properties of the total absorbent material. Therefore, where the fluid being absorbed contacts the absorbent material in a highly localized area at a rate which exceeds that which the super absorbent material can readily tolerate, much of the absorbent medium frequently is not utilized at all, thus resulting in an inefficient product.

Although the use of surfactants provides some of the properties noted above, the use of surfactants may also create additional problems. For example, certain surfactants have been stated by authorities to have potential long-term harmful characteristics, and may give rise to environmental concerns if not inactivated or degraded before being released into the environment. Furthermore, most frequently used surfactants are not readily degradable, and thus remain surface active long after producing the desired effect on the desired surroundings. While the use of non-degradable or not readily degradable surfactants may provide certain desired properties to a substrate (i.e. reduced surface tension, enhanced or controlled penetration and/or softness), because the surfactants may be non-degradable they not only continue to attempt to impart these properties on their surroundings (including those on which it is not intended or is undesirable to do so), but may, according to authorities, also cause damage (i.e. cell destruction) in the environment long after the product incorporating them has been used, discarded and/or destroyed.

In addition to creating and/or causing environmental problems or concerns, surfactants which are not inactivated or degraded, also may produce less than desirable results if used in some products. That is, the surfactants which are not degraded or inactivated continue, at least to some degree, to impart their characteristics on surrounding fluids and surfaces after the surfactant has achieved its purpose for incorporation. For example, a surfactant is unable to distinguish between when it is desired that the surface tension of a fluid be reduced and when it is undesirable to do so. Consequently, unless degraded, inactivated, or otherwise prevented from doing so, the surfactant will continue to impart its surface tension reducing properties on surrounding fluids and the environment even where it may be undesirable to do so.

This is especially true where the surfactant has been included or incorporated in the product for the purpose of lowering the surface tension of an insulting or contacting fluid. For example, in certain applications, especially in diapers, training pants and the like, where at least some of the surfactant passes from a topsheet or liner of the diaper or training pant to a second layer but is not inactivated or degraded, rewet or backflow of the fluid intended to be removed from the wear surface may occur to some degree, thereby reducing the effectiveness of the product and/or possibly causing leakage. Rewet or backflow is frequently the result of the pressure which is generated by the wearer's actions (i.e. sitting, twisting, etc.) and by the remaining surface activity of the surfactant which has migrated into the product with the fluid (e.g. the surfactant's surface activity inside the article reduces the surface tension of the fluid contained therein and allows or encourages the movement of fluid from inside the article back to the wear surface of the article, thereby defeating the original intent of containing the fluid in the article). The inability to inactivate or degrade a surfactant often reduces the effectiveness of the product, and especially personal care products. Furthermore, as above, the presence of an active surfactant in an absorbent material adversely effects the wicking properties or capillary action (as expressed by Laplace's equation) of the material.

Although some surfactants are known to be degradable, such as those disclosed in U.S. Pat. No. 5,527,560 of Fereshtehkhou et al., U.S. Pat. No. 5,427,696 of Phan et al., U.S. Pat. No. 5,312,522 of Phan et al., and U.S. Pat. No. 5,274,159 of Pellerite et al., these surfactants typically are used as softeners and detergents. The use of pH degradable surfactants in personal care product applications is not known. Furthermore, the surfactants developed as detergents and softeners depend on temperature for their degradability characteristics that are due, presumptively in part, to the fact that a range of temperatures can be expected in the environment or in the environment they are intended to be used in, whereas a specific range of pH cannot be accurately controlled, projected or expected to occur in the environment. Those surfactants which are known to be pH degradable are used in water treatment stations; however, those surfactants do not degrade substantially immediately and are part of a homogeneous solution where the pH of the entire solution is substantially uniform. (See "TRITON SP-Series Surfactants" pamphlet UC-1492, published by Union Carbide Corporation.) It is not known to use pH degradable surfactants in heterogeneous composites.

Thus, there is a need for a surfactant or class of surfactants which provides the desired wetting, spreading, emulsifying, dispersing, penetrating, and/or adhesion properties on the surface of the substrate to which the surfactant is applied, yet becomes inactivated or is degraded immediately upon or soon after contact with or passing into another layer or portion of the substrate. There is also a need for a method of degrading or inactivating a surfactant wherein the method is not temperature dependent. Additionally, there is a need for a method of inactivating or degrading a surfactant through the use of an acidic or a basic material, such that when a suitable surfactant and a suitable acidic or basic material are incorporated into a composite or product, the surfactant acts to lower the surface tension of a fluid on the surface of the product so as to allow or more readily enable the fluid (and some or all of the surfactant which is carried by the fluid) to pass into the substrate, and the acidic or basic material inactivates or degrades the surfactant upon or soon after contact therewith, such that the surfactant does not substantially adversely effect the desired wicking and absorption properties of the product.

SUMMARY OF THE INVENTION

In response to the discussed difficulties and problems encountered in the prior art a new method and composite for inactivating or degrading surfactants used in connection with personal care products have been discovered. The composite not only provides for acceptable wetting and penetration of the outer surface of a substrate by a fluid, but also provides for the inactivation or degradation of the surfactant enabling greater wetting and penetration of the substrate once the surfactant passes into a second layer of the substrate. Thus, the composite is able to realize the advantages and benefits of surfactants without experiencing the adverse effects typically associated with the use thereof.

Specifically, in the present invention, one or more surfactants are incorporated into an article or product for reducing the surface tension of the fluid contacting or insulting the wear surface of the product. That is, the surfactants are generally incorporated to promote wettability and penetrability of the substrate. In use, when a substrate surface having a surfactant applied thereto is contacted by a fluid, the surfactant lowers or reduces the surface tension of the fluid and allows or more readily enables fluid penetration of the outer surface of the substrate. While providing a reduction in the surface tension of the fluid on the surface of the substrate, a portion of the surfactant typically dissolves and moves with the fluid into the substrate or article, where the surfactant is degraded or inactivated upon or soon after passing into or contacting an inner portion of the article or a second layer of the substrate. Once the surfactant is inactivated, further handling of the fluid will be made easier in that the absorption and wicking properties of the second layer of the substrate will not be adversely effected.

Furthermore, the concern of environmental contamination and the problem of rewet or backflow typically associated with surfactants in personal care products is significantly reduced. Additionally, for some applications, it is desired that the surfactant only be applied in the target zone or zones of the product or composite material. Applications which are limited to the target zone further reduce the amount of non-degraded or non-inactivated surfactant which is introduced in to the environment or other surroundings once the product is discarded or otherwise disposed of. That is, surfactant which might have been applied to the composite material, but which would not have passed into the second layer of the substrate, because a lack of contact with the contacting or insulting fluid, and which would otherwise have remained surface-active when introduced into the environment or other surroundings upon disposal will not get released into the surroundings at a later time where it might have a detrimental effect. Targeted application of the surfactant will also further reduce flowback or rewet concerns where the second layer of the substrate is not separated by an optional third layer (i.e. a second layer of a liner or a second surge layer).

The present invention relates to a composite material that includes a substrate, and a surfactant, wherein the substrate has at least a first layer and a second layer, the first layer having a first surface and a second surface, and wherein the surfactant is applied to the first layer of the substrate. The surfactant acts to lower the surface tension of a fluid which contacts the first layer of the substrate such that the contacting fluid is allowed or more readily enabled to pass through the first layer of the substrate, but such that the surfactant does not substantially adversely effect the absorption capacity or wicking height of the second layer of the substrate, as the second layer of the substrate substantially inactivates the surfactant. That is, once the surfactant passes through the first layer of the substrate, the surfactant is inactivated or degraded, or substantially so, such that the surface tension within the substrate increases thereby encouraging the fluid to pass into or through the second layer of the substrate. To enhance absorption of the composite material, it is contemplated that the second layer of the substrate is or comprises an absorbent core, such as a superabsorbent material or pulp. It is also contemplated that the second layer of the substrate is basic or acidic, in that upon contact with the second layer of the substrate, the fluid will have a pH in the range from about 1 to about, but not equal to, 7, more desirably from about 2 to about 6, and most desirably from about 3 to about 5. Alternatively, the second layer of the substrate may be basic having a pH in the range from about, but not equal to, 7 to about 14, more desirably from about 8 to about 12, and most desirably from about 9 to about 11. Although not limited thereto, the surfactant applied to the substrate is desirably chosen from the a class of surfactants having a disulfide bond, a ketal group or a siloxal group.

The present invention is further directed to a composite material including a substrate and a surfactant, the substrate having at least a first layer and a second layer, the first layer having a first surface and a second surface, the surfactant being applied to the first layer of the substrate. The composite material has properties such that when a fluid having a first surface tension contacts the first layer of the substrate, the surfactant acts to lower the surface tension of the fluid to a second surface tension, so as to permit or more readily enable the fluid to pass through the first layer of the substrate. Once the fluid having a reduced surface tension has passed through the first layer and into the second layer of the substrate, the surfactant in the substrate begins to inactivate or degrade causing the surface tension of the fluid in the substrate to increase to a third surface tension. In this embodiment it is desired that at a time 24 hours after the fluid having the first surface tension contacts the surfactant, the third surface tension of the fluid is at least 5 dynes/cm greater than the lowest second surface tension which is experienced by the fluid, more desirably at least 10 dynes/cm greater than the lowest second surface tension experienced by the fluid, more desirably at least 20 dynes/cm greater than the lowest second surface tension experienced by the fluid, and most desirably at least 30 dynes/cm greater than the lowest second surface tension experienced by the fluid. As with the other embodiments of the present invention described above, this substrate of this embodiment may be selected from woven fabrics, knit fabrics, nonwoven fabrics, foams, film-like materials and paper materials. It is further contemplated that the composite material of this embodiment may comprise a personal care product or component thereof, as well as a sorbent, wiper, or component thereof, or the like.

The invention is also directed to a method for forming a composite material adapted for inactivating surfactants upon contact with a portion of a substrate. The method includes providing a substrate having at least a first layer and a second layer, applying a surfactant to the first layer of the substrate, and subjecting the substrate to at least one condition which facilitates migration of the surfactant from the first layer of the substrate to the second layer of the substrate. The alkalinity of the second layer of the substrate is non-neutral such that the non-neutral layer reacts with any of the surfactant which comes in contact therewith, such that the absorption and wicking properties of the second layer of the substrate are not substantially adversely effected by the surfactant. The alkalinity of the second layer may range in pH from about 1 to about 14, except that the pH of the second layer should not be equal to 7. The desired surfactants include, but are not limited to, those having a disulfide bond or containing a ketal or siloxal group.

The invention is also directed to a method of degrading or inactivating a surfactant once the surfactant has changed the surface tension of the contacting fluid and passed into the substrate. The method includes the provision of a substrate having at least two layers, applying a surfactant to the first layer of the substrate, insulting the first layer of the substrate with a fluid, lowering the surface tension of the fluid contacting the first layer of the substrate, allowing or more readily enabling the fluid and at least a portion of the surfactant to pass through the first layer of the substrate into the second layer of the substrate, and inactivating the surfactant when or soon after the surfactant passes into or comes in contact with the second layer of the substrate.

It is contemplated that the substrate of the composite material and methods described herein may comprise a sorbent product, a personal care product, a wiper, or one or more components thereof.

With the foregoing in mind, it is a feature and advantage of the invention to provide a composite material which has a surfactant that sufficiently reduces the surface tension of an insulting or contacting fluid so that the desired penetration of the outer surface of the composite is achieved, yet does not substantially adversely effect the desired absorption, wicking and wetting characteristics of the other layers of the substrate.

It is also a feature and advantage of the invention to provide a method of rapidly degrading or inactivating a surfactant once it has changed the surface tension of a fluid and passed into the article which the composite material comprises.

DEFINITIONS

As used herein the following terms have the specified meanings, unless the context demands a different meaning, or a different meaning is expressed; also, the singular generally includes the plural, and the plural generally includes the singular unless otherwise indicated.

As used herein, the term "composite" refers to a material which may be a multicomponent material or a multilayer material. Frequently, a composite material is the result of the combination of one or more layers of material which are selected based on their properties to create in which one layer is elastic. These materials may be, for example, "stretch bonded" laminates and "neck bonded" laminates As used herein, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

As used herein, the terms "degradation" and "inactivation" and other derivatives from the root term "degrade" or the term "inactivate" are intended to be interchangeable. Furthermore for purposes of this disclosure the use of the term "degrade" or its derivatives in conjunction with the term "inactivate" or its derivatives is not intended to suggest and should not be construed that the terms have different or contradictory meanings in some instances.

As used herein, the term "fabric" refers to all of the woven, knitted and nonwoven fibrous webs.

As used herein, the term "layer" when used in the singular can have the dual meaning of a single element or a plurality of elements.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein "multilayer laminate" or "multi-layer laminate" means a laminate wherein at least one of the layers is spunbond and at least one is meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

As used herein "multilayer substrate" or "multi-layer substrate" typically means a substrate having at least two layers. The layers of the substrate may, without limitation, include a topsheet or liner, a surge material, an absorbent layer, a backsheet, or a combination thereof. It is also intended that each of the layers may itself be multilayered. That is, for example, a topsheet or liner could be a two-layer topsheet or liner. Thus, a two-layer liner may be combined with a two-layer surge material. The layers of the substrate may be combined in any commercially recognized manner, which may, without limitation, include entanglement, adhesion, thermal bonding. The layers which comprise the substrate may be woven, non-woven, or a combination thereof, depending on the desired characteristics of the substrate. Although in most circumstances it is contemplated that the terms multilayer substrate or multi-layer substrate will mean a substrate having at least two layers, those terms are also intended to include in their meanings a two-sided single layer product, such as a wipe, wherein a surfactant could be applied to one side of the product and an inactivating or degrading agent is applied to the other.

As used herein the terms "nonwoven" and "nonwoven fabric or web" mean a web having a structure of individual fibers, filaments or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "personal care product" or "personal care absorbent product" means diapers, training pants, swim wear, absorbent underpants, baby wipes, adult incontinence products, sanitary wipes, wet wipes, feminine hygiene products, wound dressings, bandages, mortuary and veterinary wipes, hygiene and absorbent products, and the like.

As used herein, a "superabsorbent" or "superabsorbent material" refers to a water-swellable, water-soluble organic or inorganic material capable, under favorable conditions, of absorbing at least about 15 times its weight and, more desirably, at least about 30 times its weight in an aqueous solution containing 0.9 weight percent sodium chloride. Organic materials suitable for use as a superabsorbent material in conjunction with the present invention include, but are not limited to, natural materials such as guar gum, agar, pectin and the like; as well as synthetic materials, such as synthetic hydrogel polymers. Such hydrogel polymers include, for example, alkali metal salts of polyacrylic acids, polyacrylamides, polyvinyl alcohol, ethylene, maleic anhydride copolymers, polyvinyl ethers, methyl cellulose, carboxymethyl cellulose, hydroxypropylcellulose, polyvinylmorpholinone, and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres and the like. Typically the superabsorbent material is present within the absorbent body in an amount from about 5 to about 95 weight percent based on total weight of the absorbent body. Superabsorbents are generally available in particle sizes ranging from about 20 to about 1000 microns. An example of a suitable commercially available superabsorbent is SANWET IM 3900 available from Hoescht Celanese located in Portsmouth, Va. and DRYTECH 2035LD available from Dow Chemical Co. located in Midland, Mich.

As used herein, the terms "surfactant" or "surface-active agent" mean any compound that reduces surface tension when dissolved in water or water solutions, or which reduces interfacial tensions between two liquids, or between a liquid and a solid.

As used herein, the term "surface tension" means in any liquid, the attractive force exerted by the molecule below the surface upon those at the surface/air interface, resulting from the high molecular concentration of a liquid compared to the low molecular concentration of a gas. An inward pull, or internal pressure, is thus created, which tends to restrain the liquid from flowing. The higher the surface tension, the more resistant the molecules are to flow. For example, polar liquids such as water (about 72 dynes/cm at 20° C.), have higher surface tensions and are more resistant to flow than non-polar liquids, such as benzene (29 dynes/cm), which have lower surface tension values. Surface tension may be measured by a du Nouy tensiometer or by any other method recognized by one skilled in the art.

These terms may be defined with additional language in the remaining portions of the specification.

DETAILED DESCRIPTION OF THE INVENTION

Composites and methods are provided by the present invention for the degradation or inactivation of surfactants applied to products, especially personal care products, once the surfactants have reduced the surface tension of a fluid on an outer surface of the composite and passed, at least in part, with the fluid into a second layer of the composite. This is achieved by applying a surfactant to a substrate, insulting a first layer of the substrate with a fluid, lowering the surface tension of the fluid contacting the first layer of the substrate, allowing or more readily enabling the fluid and at least a portion of the surfactant to pass into a second layer of the substrate, and inactivating the surfactant when or soon after it comes in contact with or passes into the second layer of the substrate.

More specifically, according to the present invention, this is achieved by providing a substrate having at least a first layer and a second layer, applying a surfactant to the first layer of the substrate, and subjecting the substrate to at least one condition which facilitates migration of the surfactant from the first layer of the substrate to the second layer of the substrate. The alkalinity of the second layer of the substrate is non-neutral such that the non-neutral layer reacts with any of the surfactant which comes in contact therewith, such that the absorption and wicking properties of the second layer of the substrate are not adversely effected by the surfactant. The alkalinity of the second layer may range in pH from about 1 to about 14, except that the pH of the second layer should not be equal to 7. The desired surfactants include, but are not limited to, those having a disulfide bond or containing a ketal group, siloxal group or the like.

The new composites and methods allow for the rapid degradation or inactivation of the surfactants after the surfactants have performed their desired functions and passed into the substrate of the composite. Although allowing for immediate degradation or inactivation, depending on the surfactants and the strength of the acid or base used to degrade or inactivate the surfactant, the surfactants typically degrade or are inactivated in about 120 minutes or less, which is substantially faster than the methods or techniques currently used. Furthermore, unlike the prior art, the new composites and methods do not depend on exposure to certain temperatures for the degradation of the surfactant to occur. This substantially immediate, non-temperature dependent degradation or inactivation not only reduces or eliminates the chance the surfactants may be released to the environment prior to degradation or inactivation, but also significantly reduces the backflow or rewet concerns which arise from surface active agents which pass into the substrate yet are not quickly degraded or inactivated, if at all. The rewet concerns are reduced as the by-products produced by the degradation of the surfactant are not surfactants (i.e. are not surface active) and do not act to reduce the surface tension of the fluids surrounding them, and as such the surface tension of the fluid containing the by-products is able to return to its original value and does not readily encourage flow of the fluid in the substrate to the surface of the substrate. Thus, but for extreme circumstances (i.e. excessive pressure, twisting or weight exerted on the substrate), rewet concerns are essentially eliminated. A liner having two or more layers will further reduce rewet concerns. The present invention also contemplates that the surface tension of the contacting or insulting fluid will increase after passing into the second layer of the substrate, but may not achieve the same level as that of the contacting or insulting fluid prior to contacting the surfactant. The difference in surface tension between that of the fluid prior to contacting the surfactant and the surface tension of the fluid within the second layer of the substrate may be attributed to the amount of surfactant which continues to pass into the substrate, or the inclusion of a weak acid or base in the second layer of the substrate, the inclusion of an amount of acid or base in the substrate which is insufficient to completely inactivate or degrade the surfactant which passes into the second layer of the substrate; however, while the desired embodiment of the present invention will completely inactivate or degrade the surfactant, the incomplete inactivation or degradation of the surfactant which passes into the substrate is contemplated by the present invention and may be desired in some circumstances. Additionally, to further prevent the passing of non-degraded or non-inactivated surfactant into the environment or other surroundings upon disposal, in a desired embodiment of the present invention, the surfactant is applied only to the expected target zones of the composite material.

Figure 1:
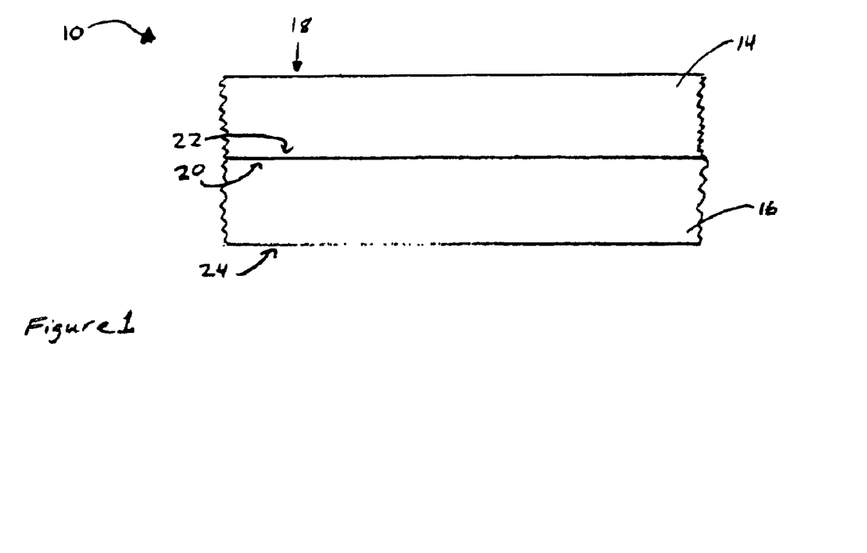
FIG. 1 is a cross-sectional view of one embodiment of a composite material in accordance with the present invention.

FIG. 1 illustrates the simplest form of the composite material which is the present invention. As shown, the composite material comprises a substrate 12, said substrate having a first layer 14 and a second layer 16, said first and second layers having a first surface 18, 20, and a second surface 22, 24 opposite the first surface, respectively. The second surface 22 of the first layer 14 of the substrate 12 being next to the first surface 20 of the second layer 16 of the substrate. The composite further comprises a surfactant (not shown) applied to the first layer 14 of the substrate.

Figure 2:
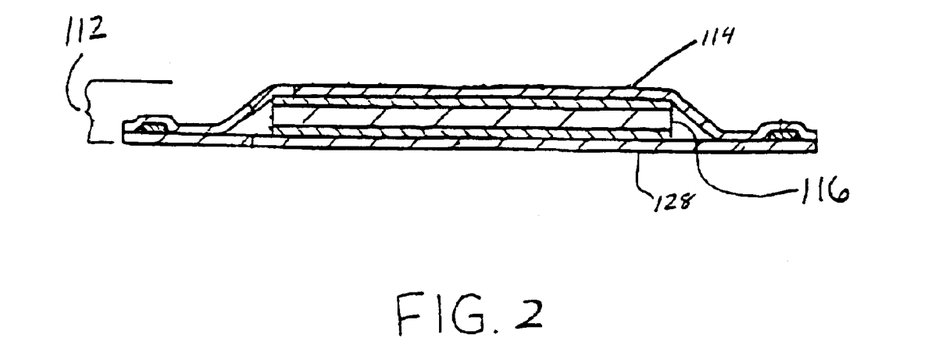
FIG. 2 representatively shows a sectional view of the composite material according to another embodiment of the present invention, wherein the composite material is part of a personal care product.

FIG. 2 is a representative sectional view of an integral absorbent garment article or personal care product, such as disposable diaper, according to one embodiment of the present invention. As illustrated, the desired embodiment of FIG. 2 includes a substrate 112 which further includes a first layer 114, more specifically, a liquid permeable liner or topsheet, a second layer 116, more specifically an absorbent body or core comprising a superabsorbent material, and a vapor permeable backsheet or outercover 128. As shown, the second layer of the substrate can itself be comprised of multiple layers. The desired embodiment illustrated in FIG. 2 also includes a surfactant (not shown) which is applied to the topsheet 114.

As illustrated, the liquid permeable liner or topsheet 114 is positioned in facing relation with the vapor permeable backsheet or outercover 128. The absorbent body 116, such as an absorbent pad, is located between the backsheet 128 and the topsheet 114. The backsheet 128 and topsheet 114 are intended to face the garment and body of the wearer, respectively, while in use.

The various components of the substrate 112 may be integrally assembled together employing various types of suitable attachment means, such as adhesive, sonic bonds, thermal bonds or combinations thereof. In the shown embodiment, for example, the topsheet 114 and backsheet 128 may be assembled to each other and to the absorbent body 116 with lines of adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive.

The permeability of the backsheet is configured to enhance the breathability of the absorbent article to reduce the hydration of the wearer's skin during use without allowing excessive condensation of vapor, such as urine, on the garment facing surface of the backsheet 128 which can undesirably dampen the wearer's clothes.

As above, the first layer 114 of the substrate 112 is treated with a surfactant. This is done to promote wettability of the substrate, thereby promoting the wicking of moisture away from the surface of the user's skin and improved skin health conditions.

In one embodiment, the fabric of the topsheet 114 is surface treated with a surfactant such as that commercially available from Union Carbide Chemicals and Plastics Company, Inc., of Danbury, Conn., U.S.A. under the trade designation TRITON X-102. Alternatively, the fabric may be surface treated with about 0.3 weight percent of a surfactant mixture which contains a mixture of AHCOVEL Base N-62 and GLUCOPON 220 UP surfactant in a 3:1 ratio based on a total weight of the surfactant mixture. The AHCOVEL Base N-62 is purchased from Uniqema Inc., a business having offices in New Castle, Del., and includes a blend of hydrogenated ethoxylated castor oil and sorbitan monooleate. The GLUCOPON 220 UP is purchased from Cognis Corporation, a business having offices in Ambler, Pa., and includes alkyl polyglycoside. The surfactant may be applied by any conventional means, such as spraying, printing, brush coating or the like. The surfactant may be applied to the entire topsheet 114 or may be selectively applied to particular sections of the topsheet 114, such as the medial section along the longitudinal centerline of a diaper or other personal care product, to provide greater wettability of such sections.

In practice, a fluid, such as urine, menses, or sweat, insults the topsheet 114 of the composite material 110 comprising the personal care product. If a surfactant is not present and the topsheet is generally non-wettable or has a low wettability, the surface tension of the fluid will often cause the fluid to pool on the surface of the topsheet. While most fluids will pass through the topsheet of an absorbent care article, some with more difficulty than others, the pooling concentrates the fluid in one area of the composite and generally results in less than maximum absorption efficiency for the second layer of the substrate. If the second layer of the substrate contains a superabsorbent material, the concentration of the fluid in one area of the composite generally results in gel blocking which limits the absorbency efficiency of the substrate as well as producing undesired swelling of the second layer of the substrate. The use of a surfactant reduces the surface tension of the insulting fluid and allows or more readily enables the fluid to spread out over a greater area of the topsheet 114. The reduction in surface tension of the fluid also decreases the fluid's resistivity to penetrating the topsheet 114. In those instances where it is anticipated that multiple fluid insults or contacts may occur, it is desired that at least some of the surfactant will remain on the first layer of the substrate after the fluid has passed into the second layer of the substrate, so that surfactant is available to aid in the migration of the fluid in the event future insults or contacts occur.

In addition to contributing the properties described above, the surfactants of the present invention are capable of degradation or inactivation upon contacting or passing into the second layer 16 of the substrate 12. This degradation or inactivation desirably occurs so as not to detrimentally effect the absorption capacity and wicking properties of the second layer 16 of the substrate, however, the degradation or inactivation need not occur immediately, but should occur faster than conventional surfactants that are temperature dependent. It is desirable for the surfactants of the present invention to be degraded or inactivated in less than about 120 minutes after contact with the contacting or insulting fluid, more desirably less than about 60 minutes, and most desirably within about five to about thirty minutes. Timing is important for effective utilization of the absorbent properties of the second layer 16 of the substrate 12, in that the longer an active surface agent is in an absorbent material the greater the chance of undesired swelling, rewet, less than maximum wicking and absorption efficiency and/or gel blocking. For example, if a superabsorbent material is used in or as the second layer of the substrate, rapid or substantially immediate degradation will limit the amount of gel blocking which occurs because the non-degraded surfactant will allow the fluid to be absorbed into the superabsorbent particles faster than that of a fluid which contains no surfactant. Furthermore, as a superabsorbent particle swells it forms a gel which tends to block flow of fluid into and around the particle. Therefore, if the particle has swollen to capacity and the gel from the particle has been formed such that fluid cannot pass into or around the particle, then the fluid will often pool above the area which is blocked by the gel. Further still, where gel blocking has occurred, the material which fluid would otherwise access through the gelled portion of material will have to find an alternative route to that material or it will not be used. In either event the efficiency of the absorbency of the material has been reduced. Thus, the faster the surfactant is degraded, the quicker the surface tension of the fluid in the substrate approaches the surface tension of the fluid prior to contacting the surfactant on the surface of the first layer of the substrate. The closer the surface tension of the fluid in the substrate is to the original surface tension of the fluid prior to contact with the surfactant, the less surface active agent or surfactant which is present and consequently the less effect the surfactant will have on the absorption and wicking properties of the second layer of the substrate. Thus, the extent of the adverse effects on wicking and absorption properties are reduced.

It is desired that the surfactants of the present invention be subject to acid or basic hydrolysis and may be selected from a class of surfactants having a disulfide bond or those containing a ketal group, siloxal group or the like.

In this embodiment, it is critical that the surfactants be readily cleavable by an acid or a base and which produce non-surface-active by-products when degraded or inactivated.

In one embodiment of the present invention, the desired surfactants are subject to acid hydrolysis. As above, when a fluid insults the product comprised of the composite material, the surfactant on the surface of the substrate lowers the surface tension of the fluid. During the insult and reduction in surface tension of the fluid, some of the surfactant dissolves in the fluid and migrates with the fluid through the topsheet 114 of the substrate 112. Upon passing through the topsheet 114, the surfactant is exposed to the second layer 116 of the substrate 112. In a desired embodiment of the present invention, the second layer of the substrate is an absorbent core material which is acidic in nature. In a more desired embodiment the absorbent is a pulp material and is highly acidic. It is desirable for the absorbent core comprising the second layer of the substrate to have a pH in the range between about 1 and about, but not equal to, 7. It is more desirable that the absorbent core of the second layer of the substrate have a pH in the range from about 2 to about 6. It is most desirable that the absorbent core of the second layer of the substrate have a pH in the range from about 3 to about 5. For purposes of this description, reference to the pH of the second layer of the substrate is intended to refer to the pH of the fluid which results once an aqueous fluid contacts the non-neutral second layer. When the surfactants contact or otherwise interact with the acidic second layer 116, the surfactants undergo acid hydrolysis such that the surfactant is degraded or inactivated into two non-surface-active by-products. Desirably, the inactivation of the surfactant comprises cleaving the surfactant such that the hydrophilic head and hydrophobic tail of the surfactant are separated. For example, if the surfactant applied to the substrate is insulted with urine some of the surfactant will dissolve and migrate to the second layer of the substrate. Upon reaching the acidic second layer, the surfactant will undergo cleavage by hydrolysis, thereby degrading or inactivating the surfactant. The reaction shown below is only intended to provide an example of a hydrolysis reaction which a suitable surfactant may experience or undergo in accordance with the present invention, and is not intended to limit the scope of the invention in any manner.

EQUATION 1

EQUATION 2

X = Halogen(Iodine, choride, etc.)

As illustrated, the end result of the hydrolysis reaction is two non-surface-active by-products which may be more readily handled with the fluid in the personal care product. That is, because the by-products are no longer surface active, they will not adversely impact the wicking properties or capillary action (as expressed by Laplace's equation) of the second layer of the substrate, nor will they pose environmental concerns, as a result of their surface activity, if released to the environment when the product is disposed of.

Although desired, the acid available for such reactions need not be contained in the absorbent material. Rather, the acid necessary to inactivate or degrade the surfactant could be distributed on the surface of small inert particles contained within the absorbent. For example, a desired acid such as citric acid, could be included in the absorbent material of the article by coating. When the surfactant comes in contact with the acid in or on the second layer of the substrate, the acid initiates a hydrolysis reaction with the surfactant which has passed into or come in contact with the second layer of the substrate.

Furthermore, the second layer 16 of the substrate 12 need not be acidic and the surfactants included in the composite material of the present invention are not limited to degradation or inactivation by acid hydrolysis. An alternative embodiment of the present invention includes a basic second layer of the substrate which would enable basic hydrolysis. In this alternative embodiment of the present invention, the second layer of the substrate will be an absorbent which is basic in nature. In the desired alternative embodiment the second layer of the substrate has a pH between about, but not equal to, 7 and about 14. In a more desirable embodiment the absorbent core of the second layer of the substrate has a pH from about 9 to about 12. In a even more desirable embodiment of the present invention having a basic second layer of substrate, the pH of the second layer of the substrate will be in the range from about 9 to about 11.

Accordingly, a hydrolysis reaction similar to that described above for acid systems can also be carried out with some surfactants which are subjected to basic hydrolysis. For example, the desired surfactants to be used with a basic second layer of substrate in accordance with the present invention may include siloxane-based surfactants. While some suitable surfactants may be more desirable than others, the desired results of the present invention may be achieved so long as the surfactants used therein contain at least one readily cleavable bond which permits degradation or inactivation of the surfactant and which results in non-surface active by-products.

An example of the hydrolysis reaction which a suitable surfactant subject to basic hydrolysis is likely to experience is shown below. As with the hydrolysis reaction shown above, the surfactant is cleaved and the resulting by-products are non-surface-active.

Similarly, the base used to trigger the hydrolysis reaction may be distributed on the surface of small inert particles within the absorbent or may be contained in the absorbent itself (i.e. within the pulp fiber).

It is also preferred that the desired embodiments of the present invention each include an amount of acid or base sufficient to inactivate or degrade all of the surfactant which may be applied to the substrate. The inclusion of a sufficient amount of acid or base in or on the second layer of the substrate provides that the desired reduction in surface tension of the contacting fluid as well as the desired rate of fluid flow into the substrate may be achieved while ensuring that the surfactant does not substantially adversely effect the absorption or wicking properties of the second layer of the substrate once it passes into the substrate.

Although one of the desired means of degrading or inactivating the surfactants comprises cleaving, the scope of the invention includes any prodegradent compound or formulation that can cleave or otherwise convert a surfactant molecule into non-surface-active by-products. Examples of other means of splitting or degrading and inactivating the surfactant include the use of an enzyme or catalyst to accelerate the degradation or inactivation of the surfactant.

The invention is also directed to a method for forming a composite material adapted for inactivating surfactants upon contact with a portion of a substrate. The method includes the provision of a substrate having at least a first and a second layer, the application of a surfactant to the first layer or topsheet of the substrate, and subjecting the substrate to at least one condition which facilitates migration of the surfactant from the first layer of the substrate to the second layer of the said substrate, wherein the second layer of the substrate has a non-neutral pH, and said non-neutral second layer reacts with any of said surfactant which passes into or comes in contact with the second layer of the substrate, such that the absorption and wicking properties of the second layer of the substrate are not substantially adversely effected by the surfactant. It is desired, although not required, that the inactivation of the surfactant occur immediately after the surfactant passes through the first layer of the substrate.

One desired embodiment of the composite material formed by the method claimed herein provides for the inactivation of surfactants upon interaction of the surfactant with an acidic pulp absorbent. In use, this embodiment will include a multilayered substrate having a suitable cleavable surfactant, such as those having disulfide, ketal group, siloxane group or the like applied to the first layer of the substrate. During use of this desired composite material, it is likely that the first layer of the substrate will be insulted with an aqueous fluid, that the surfactant will lower the surface tension of the fluid such that the fluid penetrates the first layer of the substrate at the desired rate, that a portion of the surfactant will also pass through the first layer of the substrate into the second layer which comprises a highly acid superabsorbent such as pulp, and that the surfactant which passes through the first layer will be inactivated by acid hydrolysis as the surfactant contacts or enters the second layer of the substrate.

Although it is desired for the second layer of the substrate to have a non-neutral pH, another embodiment of the present invention provides for a non-neutral additive, such as an acid or base, to be applied to the second layer of the substrate. The non-neutral additive which is used to trigger the degradation or inactivation of the surfactant may be applied in any commercially known or recognized manner, including, but not limited to, saturation, spraying and printing.

Although some of the detailed description is made in the context of a disposable diaper article which is adapted to be worn by infants about the lower torso, it is readily apparent that the composite material of the present invention would also be suitable for use as or in other types of absorbent articles, such as feminine care pads, incontinence garments, training pants, industrial or domestic sorbents or wipers, and the like. It should be appreciated that alternative arrangements of the invention can comprise any combination of such configurations, including those absorbent articles or personal care products whose substrate is comprised of more than two layers. As such, the use of a desired embodiment, for ease in understanding and describing the invention shall not, in any manner, limit the scope of the invention.

While the present invention has been described in connection with certain desired embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A composite material comprising:
   a substrate, said substrate comprising at least a first layer and a second layer, said first layer having a first surface and a second surface; and
   a surfactant applied to the first layer of the substrate;
   wherein the surfactant lowers the surface tension of a fluid which contacts the first layer of the substrate, but does not substantially adversely effect the absorption capacity or wicking height of the second layer of the substrate and the second layer of the substrate is acidic or basic and substantially inactivates the surfactant.

2. The composite material of claim 1, wherein the first layer of the substrate is a nonwoven.

3. The composite material of claim 1, wherein the second layer of the substrate is an absorbent core.

4. The composite material of claim 1, wherein the second layer of the substrate is a superabsorbent material.

5. The composite material of claim 1, wherein the second layer of the substrate is comprised of pulp.

6. The composite material of claim 1, wherein the second layer of the substrate is acidic.

7. The composite material of claim 1, wherein the second layer of the substrate is basic.

8. The composite material of claim 6, wherein the second layer of the substrate has a pH of less than about 6.

9. The composite material of claim 6 wherein the second layer of the substrate has pH in the range from about 1 to 6.

10. The composite material of claim 6, wherein the second layer of the substrate has pH in the range from about 2 to about 6.

11. The composite material of claim 6, wherein the second layer of the substrate has pH in the range from about 3 to about 5.

12. The composite material of claim 7, wherein the second layer of the substrate has pH in the range from 8 to about 14.

13. The composite material of claim 7, wherein the second layer of the substrate has pH in the range from about 8 to about 13.

14. The composite material of claim 7, wherein the second layer of the substrate has pH in the range from about 9 to about 12.

15. The composite material of claim 1, wherein the surfactant does not substantially adversely effect the absorption rate of the second layer of the substrate.

16. The composite material of claim 1, wherein the surfactant does not substantially adversely effect the wicking height of the second layer of the substrate.

17. The composite material of claim 1, wherein the surfactant is applied only to the first layer of the substrate.

18. The composite material of claim 1, wherein the surfactant is selected from a class of surfactants having a disulfide bond or those containing a ketal group or a siloxal group.

19. A personal care product comprising the composite material of claim 1.

20. The personal care product of claim 19, wherein the personal care product is selected from a diaper, training pant, absorbent underpant, adult incontinence product, sanitary wipe, wet wipe, feminine hygiene product, wound dressing, bandage, and mortuary and veterinary wipe, hygiene and absorbent product.

21. An absorbent product comprising the composite material of claim 1.

22. The absorbent product of claim 21, wherein the absorbent is selected from a sorbent or wiper.

23. A multi-layered substrate with a surfactant applied thereto, said surfactant selected from the group consisting of a class of surfactants having a disulfide bond, a ketal group, or a siloxal group,
   wherein said surfactant lowers the surface tension of fluids contacting the substrate to which the surfactant is applied such that fluid intake into the substrate is not substantially adversely effected, and such that the surfactant is substantially inactivated upon contacting second layer of the substrate that is acidic or basic.

24. The multi-layered substrate of claim 23, wherein the substrate comprises a personal care product or component thereof.

25. The multi-layered substrate of claim 24, wherein the personal care product is selected from a diaper, training pant, absorbent underpant, adult incontinence product, sanitary wipe, wet wipe, feminine hygiene product, wound dressing, bandage, and mortuary and veterinary wipe, hygiene and absorbent product.

26. A composite material comprising:
   a substrate, said substrate having at least a first layer and a second layer, said first layer having a first surface and a second surface; and
   a surfactant applied to the first layer of the substrate;
   wherein the second surface is acidic or basic;
   wherein the composite material has properties such that when a fluid having a first surface tension contacts the first layer of the substrate, the surfactant acts to lower the surface tension of the fluid to a second surface tension; and
   wherein once the fluid having a reduced surface tension has passed through the first layer and into the second layer of the substrate, the surfactant in the substrate begins to inactivate or degrade causing the surface tension of the fluid in the substrate to increase to a third surface tension.

27. The composite material of claim 26, wherein at a time 24 hours after the fluid having the surface tension contacts the surfactant, the third surface tension of the fluid is at least 6 dynes/cm greater than the lowest second surface tension which is experienced by the fluid.

28. The composite material of claim 26, wherein the third surface tension of the fluid is at least 10 dynes/cm greater than the second surface tension of the fluid at a time 24 hours after the fluid having the first surface tension contacts the surfactant.

29. The composite material of claim 26, wherein the third surface tension of the is at least 20 dynes/cm greater than the second surface tension of the fluid at a time 24 hour after the fluid having the first surface tension contacts the surfactant.

30. The composite material of claim 26, wherein the third surface tension of the fluid is at least 30 dynes/cm greater than the second surface tension of the fluid at a time 24 hours after the fluid having the first surface tension contacts the surfactant.

31. The composite material of claim 26, wherein the substrate is selected from woven fabrics, knits fabrics, nonwoven fabrics, foams, film-like materials and paper materials.

32. The composite material of claim 26, wherein the first layer of the substrate is a liner or topsheet.

33. The composite material of claim 26, wherein the first layer of the substrate comprises a nonwoven web.

34. The composite material of claim 26, wherein the second layer of the substrate is an absorbent core material.

35. The composite material of claim 26, wherein the second layer of the substrate is a superabsorbent material.

36. The composite material of claim 26, wherein the second layer of the substrate contains pulp.

37. The composite material of claim 26, wherein the second layer of the substrate is acidic.

38. The composite material of claim 26, wherein the second layer of the substrate is basic.

39. The composite material of claim 26, wherein the second layer of the substrate has a pH in the range between of from about 1 to 6.

40. The composite material of claim 26, wherein the second layer of the substrate has a pH in the range from about 2 to about 6.

41. The composite material of claim 26, wherein the second layer of the substrate has a pH in the range from about 3 to about 6.

42. The composite material of claim 26, wherein the second layer of the substrate has a pH in the range of from 8 to about 14.

43. The composite material of claim 26, wherein the second layer of the substrate has a pH in the range from about 8 to about 13.

44. The composite material of claim 26, wherein the second layer of the substrate has a pH in the range from about 9 to about 12.

45. The composite material of claim 26, wherein the surfactant may be applied to the entire first layer of the substrate or only a portion thereof.

46. The composite material of claim 45, wherein the surfactant is only applied to one surface of the first layer of the substrate.

47. The composite material of claim 26, wherein the surfactant may be selected from a class of surfactants having disulfide bond or a containing a ketal group, or a siloxal group.

48. The composite material of claim 26, wherein the substrate comprises a personal care product or component thereof.

49. The composite material of claim 26, wherein the composite material comprises a sorbent, wiper, or component thereof.

* * * * *